(12) United States Patent
Rao et al.

(10) Patent No.: US 10,612,054 B2
(45) Date of Patent: Apr. 7, 2020

(54) SINGLE-CELL FACTORY FOR EFFICIENTLY SYNTHESIZING α-AMINOBUTYRIC ACID AND CONSTRUCTION AND APPLICATION THEREOF

(71) Applicant: Jiangnan University, Wuxi (CN)

(72) Inventors: Zhiming Rao, Wuxi (CN); Junping Zhou, Wuxi (CN); Taowei Yang, Wuxi (CN); Xian Zhang, Wuxi (CN); Meijuan Xu, Wuxi (CN); CaiZhe Zhang, Wuxi (CN); Yunlong Qi, Wuxi (CN); Junxian Zheng, Wuxi (CN)

(73) Assignee: JIANGNAN UNIVERSITY, Wuxi (CN)

( * ) Notice: Subject to any disclaimer, the term of this patent is extended or adjusted under 35 U.S.C. 154(b) by 0 days.

(21) Appl. No.: 16/063,651

(22) PCT Filed: Nov. 17, 2016

(86) PCT No.: PCT/CN2016/106241
§ 371 (c)(1),
(2) Date: Jun. 18, 2018

(87) PCT Pub. No.: WO2018/090288
PCT Pub. Date: May 24, 2018

(65) Prior Publication Data
US 2019/0161779 A1 May 30, 2019

(30) Foreign Application Priority Data
Nov. 16, 2016 (CN) .......................... 2016 1 1006643

(51) Int. Cl.
| | |
|---|---|
| *C12P 13/04* | (2006.01) |
| *C12N 9/06* | (2006.01) |
| *C12P 7/40* | (2006.01) |
| *C12N 9/88* | (2006.01) |
| *C12N 15/73* | (2006.01) |
| *C12R 1/07* | (2006.01) |
| *C12R 1/19* | (2006.01) |

(52) U.S. Cl.
CPC ............ *C12P 13/04* (2013.01); *C12N 9/0016* (2013.01); *C12N 9/88* (2013.01); *C12N 15/73* (2013.01); *C12P 7/40* (2013.01); *C12Y 104/01005* (2013.01); *C12Y 403/01019* (2013.01); *C12R 1/07* (2013.01); *C12R 1/19* (2013.01)

(58) Field of Classification Search
None
See application file for complete search history.

(56) References Cited

FOREIGN PATENT DOCUMENTS

| | | |
|---|---|---|
| CN | 102212567 A | 10/2011 |
| CN | 102517351 A | 6/2012 |
| CN | 104774881 A | 7/2015 |
| CN | 105238807 A | 1/2016 |
| CN | 105255934 A | 1/2016 |

OTHER PUBLICATIONS

Tao et al. (A one-pot system for production of L-2-aminobutyric acid from L-threonine by L-threonine deaminase and a NADH-regeneration system based on L-leucine dehydrogenase and formate dehydrogenase, Biotechnol Lett (2014) 36:835-841).*

* cited by examiner

*Primary Examiner* — Suzanne M Noakes
*Assistant Examiner* — Jae W Lee
(74) *Attorney, Agent, or Firm* — IPro, PLLC

(57) ABSTRACT

The present invention discloses a single-cell factory for efficiently synthesizing α-aminobutyric acid and construction and application thereof, which belong to the technical field of microorganisms. The present invention expresses an L-threonine deaminase gene, an L-amino acid dehydrogenase gene and a dehydrogenase gene for providing cofactor NADH cycle in tandem to construct a recombinant *Escherichia coli* single-cell factory which is used for efficiently synthesizing α-aminobutyric acid. The expression level of the L-threonine deaminase is optimized and controlled by an RBS sequence, so that the problem of transformation inhibition caused by the rapid accumulation of an intermediate product ketobutyric acid is solved, moreover, the expression level of the dehydrogenase for providing cofactor NADH cycle is optimized and controlled by a promoter and an RBS sequence, consequently, the NADH regeneration rate is increased, and ultimately, yield is increased. Utilizing the single-cell factory to carry out whole-cell transformation can reduce obstacles to substances getting in and out, increase the transformation rate and promote the intracellular cycle of cofactors without requiring exogenous addition, and the cost is low. Within 20 h, the yield of the recombinant *Escherichia coli* single-cell factory in a 5 L fermentation tank is 204 $g \cdot L^{-1}$, the space-time yield is 10.2 $g \cdot L^{-1} \cdot h^{-1}$, and a practical effective strategy is provided for industrialized production.

14 Claims, No Drawings
Specification includes a Sequence Listing.

SINGLE-CELL FACTORY FOR EFFICIENTLY SYNTHESIZING α-AMINOBUTYRIC ACID AND CONSTRUCTION AND APPLICATION THEREOF

TECHNICAL FIELD

The disclosure herein relates to the field of microorganisms, and more particularly relates to single-cell factory for efficiently synthesizing α-aminobutyric acid and construction and application thereof.

BACKGROUND

Non-natural α-amino acids are a major type of amino acids which are different from 22 types of natural α-amino acids capable of being synthesized by organisms themselves. Non-natural α-amino acids have important bioactivity and physiological effects, and are applied widely in the synthesis of compounds such as polypeptides, chiral drugs and alkaloid. α-aminobutyric acid is a non-natural amino acid for inhibiting the neural information transmission of the human body, and has activity for enhancing glucose phosphatases and the effect of promoting brain cell metabolism. The α-aminobutyric acid is also an important chemical material and medical intermediate, and has been applied widely in the synthesis of drugs, such as the synthesis of the antituberculosis drug ethambutol hydrochloride and the antiepileptic drug levetiracetam, and the market is huge.

Synthesis methods for the α-aminobutyric acid mainly include three types, i.e. chemical synthesis methods, an enzymatic resolution method and an enzymatic transformation method. The chemical synthesis methods include desulphurization reaction, ammonification hydrolysis reaction, ketobutyric acid reduction, etc. Although chemical synthesis is easy to operate, reaction conditions are usually harsh and byproducts can be produced easily, and sometimes, a large quantity of organic solvents harmful to the environment needs to be utilized. For example, Jeffery E. A. et al. utilized an electrochemical method to prepare the α-aminobutyric acid, the yield was only 48 percent, and moreover, the byproduct glutamic acid existed. By contrast, a microorganism method for preparing the α-aminobutyric acid has the advantages of high specificity, mild condition, environment-friendliness, etc. Furthermore, with the development of the genetic engineering technology, the metabolic pathways of constructing recombinant microorganisms for synthesizing non-natural amino acids have been accomplished. At present, the preparation of the α-aminobutyric acid by the microorganism method is mainly based on an extracellular enzymatic transformation method, which includes carrying out enzymatic resolution preparation on racemic α-aminobutyric acid and carrying out catalytic preparation with 2-ketobutyric acid as a material by means of dehydrogenase or transaminase.

In a previous research, the inventor adopted a one-step method to prepare the α-aminobutyric acid with the bulk chemical L-threonine as a cheap substrate by means of an enzyme system composed of L-threonine deaminase, L-amino acid dehydrogenase and coenzyme regeneration system. In the process of enzymatic transformation, it was discovered that the amount of the L-threonine deaminase had to be controlled accurately, and otherwise the accumulation of an intermediate product ketobutyric acid would be caused to inhibit the transformation from the ketobutyric acid to the α-aminobutyric acid, leading to the interruption of the production of the α-aminobutyric acid by enzymatic transformation. Moreover, utilizing an enzymatic transformation system to carry out the production of the α-aminobutyric acid requires cell disruption to be carried out on three types of enzyme-producing recombinant bacteria, the process is complex, and the cost is high; furthermore, the inactivation of enzymes in the process of transformation affects the stability of transformation; and in addition, due to the loss of the cofactor, constant exogenous addition is required, further increasing the production cost of the α-aminobutyric acid. Therefore, it is necessary to find a high-efficiency, stable and low-cost method for preparing the α-aminobutyric acid.

SUMMARY

In order to solve the above-mentioned problem, the present invention provides a method which utilizes an RBS sequence to optimize and control the expression level of L-threonine deaminase, constructs a recombinant *Escherichia coli* single-cell factory by linking the L-threonine deaminase, L-amino acid dehydrogenase and dehydrogenase for providing cofactor NADH cycle onto plasmid in tandem and expressing them in *Escherichia coli* and utilizes the single-cell factory to carry out whole-cell transformation to efficiently prepare α-aminobutyric acid.

The present invention constructs a single-cell factory capable of efficiently synthesizing the α-aminobutyric acid. Mainly, an RBS is utilized to optimize and control the expression level of the L-threonine deaminase (ltd) in recombinant bacteria to control the amount of an accumulated intermediate product ketonic acid, moreover, a promoter and an RBS sequence are utilized for optimization to control the expression level of the dehydrogenase for providing cofactor NADH cycle, so that the generation rate of a cofactor NADH is controlled, finally, different RBS intensities of L-threonine deaminase and L-amino acid dehydrogenase genes and the promoter-and-RBS sequence-optimized dehydrogenase for providing cofactor NADH cycle are constructed into a recombinant co-expression vector in an *Escherichia coli* expression system and the recombinant co-expression vector is transformed into *Escherichia coli* E. *coli* BL21, and thereby different genetically engineered bacterium single-cell factories are constructed successfully. Under the condition of not adding any exogenous cofactor, these single-cell factories are utilized to carry out a whole-cell transformation method to transform a cheap substrate L-threonine to efficiently prepare the α-aminobutyric acid, and thereby a practical effective strategy is provided for the industrial production of the α-aminobutyric acid.

The first objective of the present invention is to provide a recombinant bacterium single-cell factory for efficiently synthesizing α-aminobutyric acid. The recombinant bacterium single-cell factory is obtained by transforming a recombinant co-expression vector into host bacteria; the recombinant co-expression vector is a plasmid vector linked with an L-threonine deaminase gene, an L-amino acid dehydrogenase gene and a dehydrogenase gene for providing cofactor NADH cycle in tandem; with the expression of the L-amino acid dehydrogenase gene as a benchmark, the expression level of the dehydrogenase for providing cofactor NADH cycle is controlled, so that the generation rate of a cofactor NADH is at a relatively high level, and the expression level of the L-threonine deaminase is controlled at a relatively appropriate level.

The recombinant bacterium single-cell factory can obtain a better balanced rate from L-threonine to an intermediate product ketobutyric acid and from the ketobutyric acid to α-aminobutyric acid, the accumulation of the intermediate product ketobutyric acid cannot be caused, and therefore reaction inhibition cannot be caused. Moreover, the recombinant bacterium single-cell factory does not need an exogenously added cofactor, and, in comparison with other methods, reduces the paths via which a substrate gets into or out of cells or diffuses, thus increasing the transformation rate.

In one embodiment, the control is based on, but not limited to, promoter and RBS sequence optimization, enhancer, terminator and silencer optimization or etc.

In one embodiment, the control is carried out by promoter and/or RBS sequence optimization.

A construction method for the recombinant bacterium single-cell factory includes:

(1) according to gene sequences of a promoter and the L-threonine deaminase, designing different intensities of RBS sequences to control the expression level of the L-threonine deaminase, so as to control the rate of transformation from the L-threonine to the ketobutyric acid;

(2) controlling the rate of supplying the cofactor NADH, wherein the expression level of the dehydrogenase for providing cofactor NADH cycle is mainly controlled by optimizing a promoter and an RBS sequence, so as to control the regeneration rate of the cofactor NADH; and (3) connecting the RBS-optimized L-threonine deaminase gene, the L-amino acid dehydrogenase gene, the promoters and the RBS-optimized dehydrogenase gene for providing cofactor NADH cycle in sequence to construct the recombinant co-expression vector, and transforming the recombinant co-expression vector into host bacteria to construct the genetically engineered bacterium single-cell factory.

In one embodiment, in front of the L-threonine deaminase gene, there are a promoter carried by a plasmid vector itself and an RBS sequence designed for the L-threonine deaminase gene and the plasmid vector and having expression intensity lower than that of an RBS of the plasmid vector itself; the L-threonine deaminase gene and the L-amino acid dehydrogenase gene are connected through the RBS carried by the plasmid vector itself; and in front of the dehydrogenase gene for providing cofactor NADH cycle, there area promoter designed for the dehydrogenase gene for providing cofactor NADH cycle and the plasmid vector, and an RBS sequence having expression intensity higher than or equal to that of the RBS of the plasmid vector itself.

In one embodiment, the host bacteria can be *Escherichia coli*, or can be another host, such as *Bacillus subtilis*, *Corynebacterium* or yeast.

In one embodiment, the host bacteria are *E. coli* BL21.

In one embodiment, the plasmid vector can be any one of commercially purchasable plasmid vectors or any one of reported reconstructed plasmid vectors.

In one embodiment, the L-threonine deaminase is selected from, but not limited to, *Escherichia coli*-derived L-threonine deaminase (the nucleotide sequence is Gene ID: 948287 on the NCBI).

In one embodiment, the L-amino acid dehydrogenase is selected from, but not limited to, *Bacillus*-derived L-leucine dehydrogenase (Gene ID: 1206507 on the NCBI), *Bacillus*-derived L-alanine dehydrogenase (Gene ID: 936557 on the NCBI), *Streptomyces*-derived L-valine dehydrogenase (Gene ID: 1099526 on the NCBI) and *Rhodococcus*-derived L-phenylalanine dehydrogenase (Gene ID: 4219741 on the NCBI).

In one embodiment, the dehydrogenase for providing cofactor NADH cycle is selected from, but not limited to, formate dehydrogenase of *Candida boidinii* (GenBank: KM454879.1 on the NCBI), glucose dehydrogenase of *Bacillus subtilis* (Gene ID: 938261 on the NCBI) and glucose dehydrogenase of *Pseudomonas putida* (Gene ID: 1045820 on the NCBI).

In one embodiment, the RBS sequence can be different intensities of RBS sequences.

In one embodiment, the promoter or RBS sequence is front of the L-threonine deaminase gene can be obtained by optimizing different expression systems.

In one embodiment, the promoter or RBS sequence in front of the dehydrogenase gene for providing cofactor NADH cycle can also be obtained by optimizing different expression systems.

In one embodiment, the expression systems include, but are not limited to, an *Escherichia coli* expression system, or can be a *Bacillus subtilis* expression system, a *Corynebacterium* expression system, a yeast expression system, etc.

In one embodiment, the host is *Escherichia coli*; the promoter in front of the L-threonine deaminase gene is a T7 promoter; the RBS sequence connected directly in front of the L-threonine deaminase gene is any one of sequences SEQ ID NO:1 to SEQ ID NO:6; and the L-threonine deaminase gene and the L-amino acid dehydrogenase gene are connected through an RBS with a sequence shown as SEQ ID NO:22.

In one embodiment, the promoter in front of the dehydrogenase gene for providing cofactor NADH cycle is a tac promoter, and the RBS sequence is any one of SEQ ID NO:33 to SEQ ID NO:39. Optionally, the RBS sequence is a sequence SEQ ID NO:37.

In one embodiment, the recombinant co-expression vector is constructed on the basis of a plasmid vector pET-28a; the L-threonine deaminase gene and the L-amino acid dehydrogenase gene are connected directly through the RBS carried by pET-28a itself.

The second objective of the present invention is to provide a method for synthesizing α-aminobutyric acid by fermentation, which utilizes the recombinant bacterium single-cell factory of the present invention.

In one embodiment, according to the method, after being activated, the recombinant bacterium single-cell factory is transferred into a fermentation medium, a recombinant protein is expressed by IPTG induction or directly, mycelia are collected centrifugally, and the mycelia are then utilized to produce α-aminobutyric acid by whole-cell transformation.

In one embodiment, the fermentation medium has nutritional ingredients needed by the growth of microorganisms, i.e. carbon sources, nitrogen sources, inorganic salt, a growth factor, phosphate (phosphorus source), sulfate (sulfur source), etc.; the carbon sources include glucose, glycerol, etc.; the nitrogen sources mainly include yeast extract, peptone, etc.; and in addition, an appropriate quantity of metal ions can also be added into the medium.

In one embodiment, the fermentation medium is TB medium, TY medium, TYG medium or GP medium.

In one embodiment, the whole-cell transformation is as follows: after being washed, the obtained mycelia are then added into 50 mM of PB buffer solution with a pH value of 7.5 for resuspension, a substrate L-threonine and formic acid or formate or glucose are then added under 30° C., and pH is controlled at about 7.5 by 20% formic acid or 1M hydrochloric acid and 5M ammonium hydroxide.

The present invention also claims the protection of the application of the recombinant bacterium single-cell factory in the synthesis of α-aminobutyric acid, ketobutyric acid or accessory products related thereto.

The α-aminobutyric acid as an important chemical material and medical intermediate has been applied widely in the synthesis of drugs, such as the synthesis of the antituberculosis drug ethambutol hydrochloride and the antiepileptic drug levetiracetam. The present invention constructs the single-cell factory composed of the recombinant L-threonine deaminase, L-amino acid dehydrogenase and dehydrogenase for providing cofactor NADH cycle for the first time, that is, due to the fact that a certain amount of ketobutyric acid will inhibit the proceeding of the transformation process, the RBS sequence is utilized to optimize and control the expression level of the L-threonine deaminase, and thereby the amount of the accumulated ketobutyric acid as the intermediate in the process of transformation can be controlled effectively; moreover, the promoter and the RBS sequence are utilized to optimize and control the expression level of the dehydrogenase for providing the cofactor NADH, optimizing the regeneration rate of the cofactor NADH; finally, the L-threonine deaminase, the dehydrogenase and the highly effective amino acid dehydrogenase are linked to the plasmid in tandem and expressed respectively in the *Escherichia coli* expression system, so that the recombinant bacterium single-cell factory is constructed, and the single-cell factory is utilized to carry out whole-cell transformation to efficiently prepare the α-aminobutyric acid. When the single-cell factory is utilized to carry out the whole-cell transformation of the L-threonine into the α-aminobutyric acid, the transformation process is easy to operate, the recombinant bacterium culture cost is low, furthermore, any cofactor does not need to be added in the process of transformation, transformation batches are stable and do not have the phenomenon of interruption, the cost is reduced while the efficiency of transformation is increased, and the present invention has important industrial application value.

DETAILED DESCRIPTION

Example 1: RBS Sequence Optimization of L-Threonine Deaminase and Construction of L-Threonine Deaminase Recombinant *Escherichia coli*

(1) The sequence of an *Escherichia coli*-derived L-threonine deaminase gene (ltd) was bonded with a T7 promoter, and RBS sequences with different expression intensities were designed according to its expression level in *Escherichia coli*, and were then sent to Sangon Biotech (Shanghai) Co., Ltd. for gene synthesis. PCR primers included primers RBS1, RBS2, RBS3, RBS4, RBS5, RBS6 containing the RBS sequences with different expression intensities (represented by underslines and bold font, and shown in SEQ ID NO:1 to SEQ ID NO:6) and terminal primers ltdR (sequences were shown in SEQ ID NO:7 to SEQ ID NO:13) of the L-threonine deaminase gene.

RBS1:
5'-GCTCTAGAAGTAACAATTTCAGCACCGTTTCTATAACCTAATATGGCTGACTCGCAACCC-3' (Xba I)

RBS2:
5'-GCTCTAGAGAAACGCAAGAATTAACTACGACAAACTCGGGAAATGGCTGACTCGCAACCC-3' (Xba I)

RBS3:
5'-GCTCTAGAACTTTCTAAATACCTCTACCTACTCTCTATAACCCATGGCTGACTCGCAACCC-3' (Xba I)

RBS4:
5'-GCTCTAGATAAAATCACATCCAATTTACTACGGAAATATCCACATGGCTGACTCGCAACCC-3' (Xba I)

RBS5:
5'-GCTCTAGATTAAGCAATAAAATATATACTTACGGTTTACAAATGGCTGACTCGCAACCC-3' (Xba I)

RBS6:
5'-GCTCTAGAAAACTTCCTCCAACACCTACGGTTCTATAAAATGGCTGACTCGCAACCC-3' (Xba I)

ltdR:
5'-CGGGATCCTTAACCCGCCAAAAAGAACCTG-3' (BamH I)

(2) The primers containing the RBS sequences with different expression intensities and the terminal primers ltdR composed primer pairs, and PCR amplification was carried out by utilizing the chromosomal DNA of *Escherichia coli* as a template, so that nucleotide sequences of the L-threonine deaminase with different expression levels could be obtained. For example, a nucleotide segment could be obtained by carrying out amplification with RBS1 and ltdR as primers, this nucleotide segment would contain the L-threonine deaminase gene, and a section of RBS sequence was connected directly in front of the L-threonine deaminase gene.

(3) The nucleotide segments of the L-threonine deaminase with different expression levels which had been obtained in the previous step were connected separately onto a plasmid vector pET-28a (Xba I and BamH I were used respectively to carry out double-restriction enzyme digestion, and connection was then conducted), so that six recombinant plasmids pET-28a-rbs1-ltd, pET-28a-rbs2-ltd, pET-28a-rbs3-ltd, pET-28a-rbs4-ltd, pET-28a-rbs5-ltd and pET-28a-rbs6-ltd were obtained, the recombinant plasmids were transformed into competent *E. coli* BL21, positive recombinant strains were screened out, and thereby recombinant L-threonine deaminase *Escherichia coli* was obtained.

(4) LB medium was utilized to activate the recombinant L-threonine deaminase *Escherichia coli* constructed in [3], and after being cultured under the conditions of 37° C. and 160 r·min$^{-1}$ overnight, the recombinant L-threonine deaminase *Escherichia coli* was transferred respectively into 100 ml of LB medium. The inoculation amount was 1%, the culture temperature was 37° C., and the rotational speed of a shaker was 160 r·min$^{-1}$. When $OD_{600}$ of the broth reached about 0.6 to 0.8, was added with IPTG with a final concentration of 1 mM, and the flasks were put into the shaker with a temperature of 16° C. for 24 hours for induced expression. The enzyme activity of the L-threonine deaminase was tested. The cultured bacterium broth was centrifuged under the conditions of 4° C. and 8000 r·min$^{-1}$ for 10 minutes, cells we collected and washed with 100 mL of 50 mM PB buffer solution with a pH value of 7.0 twice, and the recombinant *Escherichia coli* was resuspended in 10 mL of 50 mM PB buffer solution. The suspended cells were put into an ultrasonic cell disruptor to undergo cell disruption, which was stopped for 3 s after lasting for 1 s, and the working time was 10 minutes under the power of 300 W. The disrupted cell solution was extracted and centrifuged under the conditions of 4° C. and 10000 r·min$^{-1}$ for 30 min, precipitate was removed, and the enzyme activity of supernatant was assayed.

(5) L-threonine deaminase enzyme activity assay method: 0.1M PB buffer solution with a pH value of 7.5 was utilized to prepare 40 mM threonine substrate solution. 0.96 mL of substrate buffer solution was added into a cuvette, then added with 40 μL of enzyme solution and immediately mixed uniformly. The change of ketobutyric acid concentration was determined by calculating the change of the absorbance of the enzyme reaction solution under 230 nm ultraviolet light, and was then compared with a standard curve of ketobutyric acid, so that a concentration change value of the ketobutyric acid was obtained. Enzyme activity was defined as enzyme amount needed by the production of 1 μmol α-ketobutyric acid per minute.

(6) A result indicated that the enzyme activities of the recombinant L-threonine deaminase *Escherichia coli* pET-28a-rbs1-ltd/BL21, pET-28a-rbs2-ltd/BL21, pET-28a-rbs3-ltd/BL21, pET-28a-rbs4-ltd/BL21, pET-28a-rbs5-ltd/BL21 and pET-28a-rbs6-ltd/BL21 which were induced out in the LB medium were respectively 0.13 U·mL$^{-1}$, 0.34 U·mL$^{-1}$, 0.72 U·mL$^{-1}$, 2.56 U·mL$^{-1}$, 4.89 U·mL$^{-1}$ and 11.6 U·mL$^{-1}$.

Example 2: Construction of Recombinant Plasmids and Recombinant Bacteria Co-expressing L-Threonine Deaminase and 1-Amino Acid Dehydrogenase

[1] The genomic DNAs of *Bacillus cereus*, *Rhodococcus*, *Bacillus subtilis* and *Streptomyces coelicolor* were adopted as templates.

[2] According to the gene sequences of L-amino acid dehydrogenase and enzyme digestion sites on plasmid pET-28a, L-amino acid dehydrogenase gene primers were designed, including an L-leucine dehydrogenase gene of *Bacillus cereus* Bcldh (primers PBcldhF and PBcldhR), an L-phenylalanine dehydrogenase gene of *Rhodococcus* Rjpdh (primers were PRjpdhF and PRjpdhR), an L-alanine dehydrogenase gene of *Bacillus subtilis* Bsadh (primers were PBsadhF and PBsadhR) and a valine dehydrogenase gene of *Streptomyces coelicolor* Scvdh (primers were PScvdhF and PScvdhR). Primer sequences (SEQ ID NO:14 to SEQ ID NO:21) were as follows:

```
PBcldhF:
5'-CGGGATCCAAGGAGATATACATGACATTAGAAATCTTCG-3'
(BamH I)

PBcldhR:
5'-CGAGCTCTTAGCGACGGCTAATAATAT C-3' (Sac I)

PRjpdhF:
5'-CGGGATCCAAGGAGATATACATGACTCTCACCGCGGAAC-3'
(BamH I)

PRjpdhR:
5'-CGAGCTCCTACCTGGCTGCAGCGATG-3' (Sac I)

PBsadhF:
5'-CGGGATCCAAGGAGATATACATGATCATAGGGGTTCCT-3'
(BamH I)

PBsadhR:
5'-CGAGCTCTTAAGCACCCGCCACAGATG-3' (Sac I)

PScvdhF:
5'-CGGGATCCAAGGAGATATACATGGTGACCGACGTAAACGG-3'
(BamH I)
```

-continued
```
PScvdhR:
5'-CGAGCTCTCACGGCCGGGGACGGGCCT-3' (Sac I)
```

Underlined were RBS sequences carried by plasmid vectors pET-28a themselves; and the primers were named in the following way: P+strain species initials+gene name+primer direction, that is, PBcldhF represented an upstream primer which was utilized to amplify the ldh gene derived from the *Bacillus cereus*.

[3] The genomic DNAs of the *Bacillus cereus*, the *Rhodococcus*, the *Bacillus subtilis* and the *Streptomyces coelicolor* were adopted respectively as templates, PCR amplification was carried out by utilizing the above-mentioned corresponding primers, so that nucleotide segments containing the L-amino acid dehydrogenase gene were obtained, and the RBS sequence AAGGAG (shown as SEQ ID NO:22) carried by the plasmid vector pET-28a was connected directly in front of the gene.

[4] The multiple nucleotide segments containing the L-amino acid dehydrogenase gene obtained in the previous step were connected to the recombinant plasmids pET-28a-rbs1-ltd, pET-28a-rbs2-ltd, pET-28a-rbs3-ltd, pET-28a-rbs4-ltd, pET-28a-rbs5-ltd and pET-28a-rbs6-ltd constructed in embodiment 1 (the nucleotide segments and the plasmid underwent double-restriction enzyme digestion respectively by using BamH I and Sac I, and were then connected), so that recombinant plasmids pET-28a-rbs1-ltd+Bcldh, pET-28a-rbs2-ltd+Rjpdh, pET-28a-rbs3-ltd+Bsadh, pET-28a-rbs4-ltd+Scvdh, pET-28a-rbs5-ltd+Bcldh, pET-28a-rbs6-ltd+Bcldh, etc. co-expressing L-threonine deaminase and L-amino acid dehydrogenase were obtained, the recombinant plasmids were then transformed into competent *E. coli* BL21, positive recombinant strains were screened out, and thereby recombinant bacteria co-expressing L-threonine deaminase and L-amino acid dehydrogenase were obtained.

Example 3: Construction of Dehydrogenase Recombinant *Escherichia coli* for Providing Cofactor NADH Cycle and Construction of Promoter-and-RBS Sequence-Optimized Recombinant *Escherichia coli* of Formate Dehydrogenase

[1] According to the gene sequences of dehydrogenase for providing cofactor NADH cycle from different sources and enzyme digestion sites linked to plasmid pET-28a in tandem, primers were designed, including formate dehydrogenase fdh (primers PfdhF and PfdhR) of *Candida boidinii*, glucose dehydrogenase Bsglcdh of *Bacillus subtilis* (primers over PBsglcdhF and PBsglcdhR) and glucose dehydrogenase Ppglc of *Pseudomonas putida* (primers were PPpglcdhF and PPpglcdhR). PCR was carried out respectively with the corresponding primers and genomic templates, so that gene segments of the dehydrogenase for providing cofactor NADH cycle derived from the corresponding strains were obtained, the gene segments were connected to the plasmid pET-28a (the nucleotide segments and the plasmid underwent double-restriction enzyme digestion respectively by using BamH I and Sac I, and were then connected), so that recombinant plasmids pET-28a-fdh, pET-28a-Bsglcdh and pET-28a-Ppglcdh expressing the dehydrogenase for providing cofactor NADH cycle were obtained, the recombinant plasmids were then transformed into competent *E. coli* BL21, positive recombinant strains were screened out, and thereby recombinant bacteria expressing the dehydrogenase for providing cofactor NADH cycle were obtained.

For example, amplification was carried out with PBsgl-cdhF and PBsglcdhR as a primer pair and the chromosomal DNA of *Bacillus subtilis* as a template, so that a *Bacillus subtilis*-derived glucose dehydrogenase gene segment was obtained, the glucose dehydrogenase gene segment was connected to the plasmid pET-28a (the nucleotide segment and the plasmid underwent double-restriction enzyme digestion respectively by using BamH I and Sac I, and were then connected), so that a recombinant plasmid pET-28a-rbs2-Bsglcdh expressing the *Bacillus subtilis*-derived glucose dehydrogenase was obtained, the recombinant plasmid was then transformed into competent Emil BL21, positive recombinant strains were screened out, and thereby recombinant bacteria expressing the *Bacillus subtilis*-derived glucose dehydrogenase for providing cofactor NADH cycle were obtained.

Primer sequences (SEQ ID NO:23 to SEQ ID NO:32) were as follows:

```
PBsglcdhF:
5'-CGGGATCCATGTATCCGGATTTAAAAGG-3' (BamH I)

PBsglcdhR:
5'-CCCAAGCTTTTAACCGCGGCCTGCCTGG-3' (Hind III)

P28aPromaterF:
5'-ACATGCATGCCGATCCCGCGAAATTAATAC-3' (Sph I)

PBsglcdhRBgIII:
5'-GAAGATCTTTAACCGCGGCCTGCCTGG-3' (Bgl II)

PPpglcdhF:
5'-CGGGATCCATGAGCACTGAAGGTGCGAACC-3' (BamH I)

PPpglcdhR:
5'-CCCAAGCTTTTACTCGGCTAATTTGTAAG-3' (Hind III)

PPpglcdhRBgIII:
5'-GAAGATCTTTACTCGGCTAATTTGTAAG-3' (Bgl II)

PfdhF:
5'-ACCGGGATCCATGAAAATCGTTCTGGTTCTG-3' (BamH I)

PfdhR:
5'-CGCGTCGACTTATTTTTTGTCGTGTTTACC-3' (Sal I)

PfdhRBgIII:
5'-GAAGATCTTTATTTTTTGTCGTGTTTACC-3' (Bgl II)
```

[2] Taking formate dehydrogenase as an example, the following optimization could also be carried out:
a tac promoter was selected as well, and according to the tac promoter on plasmid pXMJ-19 and the gene sequence of the formate dehydrogenase, PCR primers r1FDH-1, r2FDH, r3FDH, r4FDH, r5FDH, r6FDH and r7FDH containing different intensities of RBS sequences (represented by underlines and bold font, and shown in SEQ ID NO:33 to SEQ ID NO:39) and a terminal primer pFDHRBamHI of the formate dehydrogenase gene were designed.

Primer sequences (SEQ ID NO:40 to SEQ ID NO:49) were as follows:

```
r1FDH:
5'-CCCAAGCTTGTACGCAAGAATACTTAACTACGGTTAGAGGGATGAAG

ATCGTTTTAGTC-3' (Hind III)

r2FDH:
5'-CCCAAGCTTGTCATAGAAAAATTTAACCTACGGTTACAGGGATGAAG

ATCGTTTTAGTC-3' (Hind III)

r3FDH:
5'-CCCAAGCTTCTCATAGATAGAAATAACCTACGGTTACAGGGATGAAG

ATCGTTTTAGTC-3' (Hind III)

r4FDH:
5'-CCCAAGCTTACAAATACTCTATAAAAAAAACTACGGTTAGAATAATG

AAGATCGTTTTAGTC-3' (Hind III)

r5FDH:
5'-CCCAAGCTTCTCATCTAATACAATACAAACTACGGTTAGAACAATGA

AGATCGTTTTAGTC-3' (Hind III)

r6FDH:
5'-CCCAAGCTTAATCTACAATAAATCTCACAACTACGGTTATAATAATG

AAGATCGTTTTAGTC-3' (Hind III)

r7FDH:
5'-CCCAAGCTTTGTTAAACAAGGTCCAACTACGGTTAACACAATGAAGA

TCGTTTTAGTC-3' (Hind III)

pFDHRBamHI:
5'-CGGGATCCTTATTTCTTATCGTGTTTAC-3' (BamHI)

pTacFSphI:
5'-CATGCATGCTGACAATTAATCATCGGCT-3' (Sph I)

prrnBRBgIII:
5'-GAAGATCTAGAGTTTGTAGAAACGC-3' (Bgl II)
```

The chromosomal DNA of the *Candida boidinii* was utilized as a template, the primers containing the different intensities of RBS sequences and pFDHRBamHI respectively composed a primer pair, PCR was carried out, so that multiple gene segments containing the RBS sequences and the formate dehydrogenase were obtained, the gene segments were connected to the plasmid pXMJ-19 (the nucleotide segments and the plasmid underwent double-restriction enzyme digestion respectively by using Hind III and B H I, and were then connected), so that recombinant plasmids pXMJ-19-r1fdh, pXMJ-19-r2fdh, pXMJ-19-r3fdh, pXMJ-19-r4fdh, pXMJ-19-r5fdh, pXMJ-19-r6fdh and pXMJ-19-r7fdh expressing the formate dehydrogenase were obtained, the recombinant plasmids were then transformed into competent *E. coli* BL21, positive recombinant strains were screened out, and thereby recombinant bacteria expressing the formate dehydrogenase for providing cofactor NADH cycle were obtained.

For example, amplification was carried out with r1FDH and pFDHRBamHI as a primer pair and the *Candida boidinii* genome as a template, so that a *Candida boidinii*-derived formate dehydrogenase gene segment was obtained, the *Candida boidinii*-derived formate dehydrogenase gene segment was connected to the plasmid pXMJ-19 (the nucleotide segment and the plasmid underwent double-restriction enzyme digestion respectively by using Hind III and BamH I, and were then connected), so that the recombinant plasmid pXMJ-19-r1fdh expressing the formate dehydrogenase was obtained, the recombinant plasmid was then transformed into competent *E. coli* BL21, positive recombinant strains were screened out, and thereby recombinant bacteria expressing the formate dehydrogenase for providing cofactor NADH cycle were obtained.

[3] LB medium was utilized to activate the recombinant bacteria expressing the formate dehydrogenase constructed in [1] and [2], and after being cultured under the conditions of 37° C. and 160 r·min$^{-1}$ overnight, the recombinant bacteria were transferred respectively into 100 ml of LB medium. The inoculation amount was 1%, the culture temperature was 37° C., and the rotational speed of a shaker was 160 r·min$^{-1}$. When OD$_{600}$ reached about 0.6 to 0.8, IPTG was added to a final concentration of 1 mmol·L$^{-1}$, and flasks were put into the shaker with a temperature of 16° C. for 24 hours for induced expression. A testing experiment was carried out on the enzyme activity of the formate dehydrogenase, the cultured bacterium broth was centrifuged under the conditions of 4° C. and 8000 r·min$^{-1}$ for 10 minutes, cells were collected and washed with 100 mL of 50 mM PB buffer solution with a pH value of 7.0 twice, and the recombinant *Escherichia coli* was resuspended in 10 mL of 50 mM PB buffer solution. The suspended cells were put into an ultrasonic cell disruptor to undergo cell disruption, which was stopped for 3 s after lasting for 1 s, and the working time was 10 minutes under the power of 300 W. The disrupted cell solution was centrifuged under the conditions of 4° C. and 10000 r·min$^{-1}$ for 30 min, precipitate was removed, and the enzyme activity of supernate was assayed.

[4] Formate dehydrogenase enzyme activity assay method: 0.1M PB buffer solution with a pH value of 7.5 was utilized to prepare 100 mM sodium formate substrate solution. 0.96 mL of substrate buffer solution was added into a cuvette, then added with 40 µL of enzyme solution and immediately mixed uniformly. The change of generated NADH concentration was determined by calculating the change of the absorbance of the enzyme reaction solution under 340 nm ultraviolet light, and was then compared with a standard curve of NADH, so that a concentration change value of the NADH was obtained, or enzyme activity can be figured out by utilizing a formula according to the molar extinction coefficient of the NADH. Enzyme activity was defined as enzyme amount needed by the production of 1 µmol NADH per minute.

[5] A result indicated that the enzyme activities of the recombinant bacteria pET-28a-fdh/BL21, pXMJ-19-r1fdh/BL21, pXMJ-19-r2fdh/BL21, pXMJ-19-r3fdh/BL21, pXMJ-19-r4fdh/BL21, pXMJ-19-r5fdh/BL21, pXMJ-19-r6fdh/BL21 and pXMJ-19-r7fdh/BL21 which were induced out in the LB medium were respectively 0.34 U·mL$^{-1}$, 0.12 U·mL$^{-1}$, 0.15 U·mL$^{-1}$, 0.14 U·mL$^{-1}$, 0.27 U·mL$^{-1}$, 0.56 U·mL$^{-1}$, 0.37 U·mL$^{-1}$ and 0.41 U·mL$^{-1}$. Therefore, the next step of tandem expression was carried out with the plasmid pXMJ-19-r5fdh as a gene source.

Example 4: Construction of Recombinant *Escherichia coli* Single-Cell Factories for Efficiently Synthesizing α-Aminobutyric Acid

[1] PCR amplification was carried out with pET-28a-Bsglcdh as a template and P28aPromoterF and PBsglcdhRBglII as primers, so that a T7 promoter carried by the plasmid vector pET-28a itself, an RBS carried by pET-28a itself and a nucleotide segment of *Bacillus subtilis*-derived glucose dehydrogenase were obtained; PCR amplification was carried out with pET-28a-Ppglcdh as a template and P28aPromoterF and PPplcdhRBglII as primers, so that a T7 promoter carried by the plasmid vector pET-28a itself, an RBS carried by pET-28a itself and a nucleotide segment of *Pseudomonas putida*-derived glucose dehydrogenase were obtained; and amplification was carried out with the plasmid pXMJ-19-r5fdh as a template and pTacFSphI and prrnBR-BglII as primers, so that a tac promoter carried by the plasmid vector pXMJ-19 itself, an RBS carried by pXMJ-19 itself and a nucleotide segment of *Candida boidinii*-derived formate dehydrogenase were obtained.

[2] The three nucleotide segments obtained in the previous step were connected onto pMD18-T, so that recombinant plasmids pMD18-T-promoter+Bsglcdh, pMD18-T-promoter+Ppglcdh and pMD18-T-tac-promoter+r5fdh were constructed, which were transformed into competent *E. coli* J109, and transformants were verified.

[3] The corresponding plasmids were extracted from the transformants in [2], and the plasmids and the expression vectors pET-28a-rbs1-ltd+Bcldh, pET-28a-rbs2-ltd+Rjpdh, pET-28a-rbs3-ltd+Bsadh, pET-28a-rbs4-ltd+Scvdh, pET-28a-rbs5-ltd+Bcldh and pET-28a-rbs6-ltd+Bcldh of the L-threonine deaminase and the L-amino acid dehydrogenase linked with the different RBS sequences in embodiment 2 underwent double-restriction enzyme digestion respectively by using Sph I and Bgl II, and were then connected. Connected recombinant plasmids pET-28a-rbs1-ltd+Bcldh+r5fdh, pET-28a-rbs2-ltd+Rjpdh+r5fdh, pET-28a-rbs3-ltd+Bsadh+r5fdh, pET-28a-rbs4-ltd+Scvdh+r5fdh, pET-28a-rbs5-ltd+Bcldh+r5fdh, pET-28a-rbs6-ltd+Bcldh+r5fdh, pET-28a-rbs3-ltd+Bcldh+Bsglcdh, pET-28a-rbs4-ltd+Bcldh+Bsglcdh, pET-28a-rbs5-ltd+Rjpdh+Ppglcdh and pET-28a-rbs6-ltd+Bsadh+Ppglcdh are transformed into competent *E. coli* BL21, and the strains which are verified correct by restriction enzyme digestion are recombinant *Escherichia coli* single-cell factories for synthesizing α-aminobutyric acid.

Example 5: Preparation of *Escherichia coli* Competent Cells and Transformation of Plasmid

[1] Preparation of *Escherichia coli* Competent Cells: Monoclonal *Escherichia coli* was activated in 10 ml of LB medium, and was then shaken to be cultured under 37° C. until OD600 was 0.35, so that competent cells could be prepared; the cultured bacterium solution broth was put into ice water, and was shaken gently to be cooled rapidly for about 10 min; several sterilized 1.5 ml centrifugal tubes were prepared, the bacterium solution was dispensed into the tubes, the amount of the bacterium solution loaded in each tube was 1.2 ml, and the centrifugal tubes were put into ice; the bacterium solution was centrifuged at 8000 r·min$^{-1}$ for 10 s to 20 s, and was kept still in ice water for 2 minutes, the supernatant was discarded, 400 µL of precooled 0.1M CaCl$_2$ was added, the suspension was blown and sucked gently, and was put in ice for 15 min, and this step was repeated two to three times; finally, after the bacterium solution in each tube was centrifuged and the supernatant was discarded, 80 µL of precooled 0.1M CaCl2 was added, and the suspended bacterium solution was blown and sucked gently, and was put into ice.

[2] Transformation of Plasmid: The competent cells prepared in [1] were extracted, added with a plasmid to be transformed, repetitively blown and sucked gently and put in ice for 45 min; the centrifugal tubes were placed in a water bath kettle with a temperature of 42° C. for exactly 90 s, then taken out and put rapidly into ice for 5 min; 800 µL of LB culture medium was added, gentle mixing was conducted, and culture was carried out in a shaker with a temperature of 37° C. for 1 h to 1.5 h; the cells were centrifuged for 2 min, most of the supernatant was discarded, blowing, suction and suspension were conducted again, and 200 µL of cells were taken onto a target resistant plate, put into an incubator with a temperature of 37° C. and cultured; and after transformants were grown out, the plasmid was extracted for verification.

Example 6: Fermentation Medium for Recombinant *Escherichia coli*

[1] LB medium (g·L$^{-1}$): tryptone 10, yeast extract 5 and NaCl 10.

[2] TB medium (g·L$^{-1}$): glycerol 4, tryptone 12, yeast extract 24, $K_2HPO_4$ 12.5, $KH_2PO_4$ 2.3 and $MgSO_4$ 0.2, pH 7.0-7.2.

[3] TY medium (g·L$^{-1}$): glucose 10, tryptone 10, yeast extract 5, NaCl 3, $K_2HPO_4$ 6, $KH_2PO_4$ 3, sodium citrate 1 and $MgSO_4$ 0.2, pH 7.0-7.2.

[4] TYG medium (g·L$^{-1}$): glucose 10, tryptone 10, yeast extract 5, $K_2HPO_4$ 6, $KH_2PO4$ 3, sodium citrate 1 and $MgSO_4$ 0.2, pH 7.0-7.2.

[5] GP medium (g·L$^{-1}$): glucose 30, tryptone 10, yeast extract 5, $K_2HPO_4$ 6, $KH_2PO4$ 3, sodium citrate 1 and $MgSO_4$ 0.2, pH 7.0-7.2.

Example 7: Production of α-Aminobutyric Acid by Whole-Cell Transformation Conducted by Recombinant *Escherichia coli* Single-Cell Factories Expressing Formate Dehydrogenase

[1] The recombinant *Escherichia coli* single-cell factories pET-28a-rbs1-ltd+Bcldh+r5fdh/BL21, pET-28a-rbs2-ltd+Rjpdh+r5fdh/BL21, pET-28a-rbs3-ltd+Bsadh+r5fdh/BL21, pET-28a-rbs4-ltd+Scvdh+r5fdh/BL21, pET-28a-rbs5-ltd+Bcldh+r5fdh/BL21 and pET-28a-rbs6-ltd+Bcldh+r5fdh/BL21 obtained in step [3] in embodiment 4 were activated respectively by utilizing LB medium, cultured under the conditions of 37° C. and 160 r·min$^{-1}$ overnight and then transferred respectively into 100 mL of LB medium. The inoculation amount was 1%, the culture temperature was 37° C., and the rotational speed of a shaker was 160 r·min$^{-1}$. When OD600 reached about 0.6 to 0.8, the recombinant *Escherichia coli* single-cell factories were added with IPTG with a final concentration of 1 mmol·L$^{-1}$, and were put into the shaker with a temperature of 16° C. for 24 h for induced expression. A whole-cell transformation experiment was carried out, the bacterium broths cultured in the different media were centrifuged under the conditions of 4° C. and 8000 r/min for 10 min, cells were collected and washed with 100 mL of 50 mM PB buffer solution with a pH value of 7.0, and the recombinant *Escherichia coli* was resuspended respectively in 100 mL of 50 mM PB buffer solution with a pH value of 7.5. 0.8M L-threonine, 0.8M ammonium formate and 0.1% (v/v) tween-80 were added into the system, the system was put into the shaker with a temperature of 30° C. and continues to be cultured, and in the process of culture, 20% ammonium formate or 5M ammonium hydroxide was added every 0.5 h to keep the pH of the reaction solution at 7.5. Samples were extracted at different times, centrifuged and filtered by a 0.22 μm filter membrane and then undergo HPLC analysis.

[2] HPLC analysis conditions of amino acid: 200 μL of transformation solution sample and 400 μL of derivating agent (10 mg of o-phthalaldehyde and 0.5 ml of absolute ethyl alcohol were taken and then added with 2 ml of 0.1M borax buffer solution with a pH value of 9.5 and 50 μL of 2-mercaptoethanol) were added sequentially into an EP tube and mixed uniformly, 400 μL of 0.1M $KH_2PO_4$ buffer solution was added after 2 min, time and added reagent amounts were controlled strictly, and the samples were injected. Chromatographic column: dimosoil C18 (5 μl, 250 mm×4.6 mm); mobile phase: 0.05M sodium acetate buffer solution: methyl alcohol −63:35; detector: UV Detector; detection wavelength: 338 nm; column temperature: 40° C.; sample amount: 20 μL; flow velocity: 1.0 ml·min$^{-1}$.

[3] HPLC analysis conditions of organic acid: chromatographic column: Aminex HPX-87 (300 mm×7.8 mm); mobile phase: 5 mM $H_2SO_4$; detector: UV Detector; detection wavelength: 210 nm; column temperature: 30° C.; sample amount: 10 μL; flow velocity: 0.6 ml·min$^{-1}$.

[4] An amino acid determination result indicated that the yields of α-aminobutyric acid prepared by whole-cell transformation conducted by pET-28a-rbs1-ltd+Bcldh+r5fdh/BL21, pET-28a-rbs2-ltd+Rjpdh+r5fdh/BL21, pET-28a-rbs3-ltd+Bsadh+r5fdh/BL21, pET-28a-rbs4-ltd+Scvdh+r5fdh/BL21, pET-28a-rbs5-ltd+Bcldh+r5fdh/BL21 and pET-28a-rbs6-ltd+Bcldh+r5fdh/BL21 were respectively 22.1 g·L$^{-1}$, 48.5 g·L$^{-1}$, 66.2 g·L$^{-1}$, 81.8 g·L$^{-1}$, 40.6 g·L$^{-1}$ and 39.2 g·L$^{-1}$. L-threonine residue existed in the whole-cell transformation solutions of the recombinant bacteria pET-28a-rbs1-ltd+Bcldh+r5fdh/BL21, pET-28a-rbs2-ltd+Rjpdh+r5fdh/BL21 and pET-28a-rbs3-ltd+Bsadh+r5fdh/BL21, moreover, the accumulation of the intermediate product ketobutyric acid was not detected, and this indicated that the enzyme activity of the L-threonine deaminase induced out by rbs1/rbs2/rbs3 was low, failing to meet the high-efficiency production of the α-aminobutyric acid. On the contrary, 40.7 g·L$^{-1}$ and 41.4 g·L$^{-1}$ intermediate product ketabutyric acid were detected out respectively in the whole-cell transformation solutions of the recombinant bacteria pET-28a-rbs5-ltd+Bcldh+r5fdh/BL21 and pET-28a-rbs6-ltd+Bcldh+r5fdh/BL21, and as the previous experiment had indicated that the *Bacillus cereus*-derived leucine dehydrogenase transformation rate can fully meet the rapid accumulation of the product faster, this indicated that the high expression level of the L-threonine deaminase might lead to the accumulation of the intermediate product, thus inhibiting the proceeding of transformation.

[5] The recombinant bacteria pET-28a-rbs3-ltd+Bsadh-r5fdh/BL21, pET-28a-rbs4-ltd+Scvdh+r5fdh/BL21 and pET-28a-rbs5-ltd+Bcldh+r5fdh/BL21 were activated by utilizing LB medium, cultured under the condition of 37° C. and 160 r·min$^{-1}$ overnight and then transferred respectively into 2 L of LB medium. The inoculation amount was 8%, the culture temperature was 37° C., the rotational speed was 300 r·min$^{-1}$, and the air volume was 1.0 vvm. After 2 h to 3 h of culture, IPTG with a final concentration of 0.5 mM was added, and induction temperature was decreased to 28° C.; after 16 h of induction, centrifuging was conducted at 8000 r·min$^{-1}$ under 4° C. for 10 min, and cells were collected; 5 mM PB buffer solution with a pH of 7.5 was utilized to wash the recombinant *Escherichia coli* twice, and the recombinant *Escherichia coli* was resuspended in 50 mM PB buffer solution with a pH value of 7.5, the volume of which was the same as that in culture; 1M L-threonine and 1M ammonium formate were added into the system, transformation was carried out under the conditions of 30° C. and 300 r·min$^{-1}$, and pH was regulated to 6.0 by 20% formic acid or 5M ammonium hydroxide. After 20 h of transformation, samples were extracted, centrifuged and filtered by a 0.22 μm filter membrane and then underwent HPLC analysis, and thereby the yields of obtained α-aminobutyric acid were respectively 86.2 g·L$^{-1}$, 99.6 g·L$^{-1}$ and 43.1 g·L$^{-1}$.

Example 8: Production of α-Aminobutyric Acid by Whole-Cell Transformation Conducted After Culturing Recombinant Bacteria pET-28a-rbs4-ltd+Scvdh+r5fdh/BL21 in Different Fermentation Media The recombinant bacteria pET-28a-rbs4-ltd+Scvdh+r5fdh/BL21 were activated by utilizing LB medium, cultured under the conditions of 37° C. and 160 r·min$^{-1}$ overnight and then transferred respectively into 2 L of TB medium, TY medium, TYG medium and GP medium. The inoculation amount was 8%, the culture temperature was 37° C., the rotational speed was 300 r·min$^{-1}$, and the air volume was 1.0 vvm. After 2 h to 3 h of culture, IPTG with a final concentration of 0.5 mM was added, and induction temperature was decreased to 28° C.; after 16 hours of induction, centrifuging was conducted at 8000 r·min$^{-1}$ under 4° C. for 10 minutes, and cells were collected; 50 mM PB buffer solution with a pH value of 7.5 was utilized to wash the recombinant *Escherichia coli* twice, and the recombinant *Escherichia coli* was resuspended in 50 mM PB buffer solution with a pH value of 7.5, the volume of which was the same as that in culture; 1.8M L-threonine and 1.8M ammonium formate were added into the system, transformation was carried out under the conditions of 30° C. and 300 r/min, and pH was regulated to 7.5 by 20% formic acid or 5M ammonium hydroxide. After 10 h and 20 h of transformation, samples were extracted respectively, centrifuged and filtered by a 0.22 μm filter membrane and then undergo HPLC analysis. It was discovered that the transformation rates can all reach 98% or more after 20 h of whole-cell transformation from L-threonine to α-aminobutyric acid following TB medium, TY medium, TYG medium and GP medium fermentation, however, the differences between the transformation rates were great after 10 h, and the transformation rates were respectively 68%, 46%, 49% and 64%. Because the cost of yeast extract was higher than that of glucose, it was determined that the best fermentation medium was the GP medium, the final yield of the α-aminobutyric acid reaches 181 g·L$^{-1}$, and the space-time yield was 9.05 g·L$^{-1}$·h$^{-1}$.

Example 9: Production of α-Aminobutyric Acid by Whole-Cell Transformation Conducted by Recombinant *Escherichia coli* Single-Cell Factories Expressing Glucose Dehydrogenase

[1] The recombinant *Escherichia coli* single-cell factories pET-28a-rbs3-ltd+Bcldh+Bsglcdh/BL21, pET-28a-rbs4-ltd+Bcldh+Bsglcdh/BL21, pET-28a-rbs5-ltd+Rjpdh+Ppglcdh/BL21 and pET-28a-rbs6-ltd+Bsadh+Ppglcdh/BL21 obtained in step [3] in embodiment 4 were activated respectively by utilizing LB medium, cultured under the conditions of 37° C. and 160 r·min$^{-1}$ overnight and then transferred respectively into 2 L of LB medium. The inoculation amount was 8%, the culture temperature was 37° C., the rotational speed was 300 r·min$^{-1}$, and the air volume was 1.0 vvm. After 2 h to 3 h of culture, IPTG with a final concentration of 0.5 mM was added, and induction temperature was decreased to 28° C.; after 16 hours of induction, centrifuging was conducted at 8000 r·min$^{-1}$ under 4° C. for 10 minutes, and cells were collected; 5 mM PB buffer solution with a pH of 7.5 was utilized to wash the recombinant *Escherichia coli* twice, and the recombinant *Escherichia coli* was resuspended in 50 mM PB buffer solution with a pH value of 7.5, the volume of which was the same as that in culture; 1M L-threonine and 1M glucose were added into the system, transformation was carried out under the conditions of 30° C. and 300 r·min$^{-1}$, and pH was regulated to 7.5 by 1M hydrochloric acid or 5M ammonium hydroxide. After 18 h of transformation, samples were extracted respectively, centrifuged and filtered by a 0.22 μm filter membrane and then underwent HPLC analyswas.

[2] An amino acid determination result indicated that the yields of α-aminobutyric acid prepared by whole-cell transformation conducted by pET-28a-rbs3-ltd+Bcldh+Bsglcdh/BL21, pET-28a-rbs4-ltd+Bcldh+Bsglcdh/BL21, pET-28a-rbs5-ltd+Rjpdh+Ppglcdh/BL21 and pET-28a-rbs6-ltd+Bsadh+Ppglcdh/BL21 were respectively 33.5 g·L$^{-1}$, 89.g·L$^{-1}$, 100.2 g·L$^{-1}$ and 27.8 g·L$^{-1}$. The accumulation of the intermediate product ketobutyric acid was not detected in the whole-cell transformation solutions of the recombinant bacteria pET-28a-rbs3-ltd+Bcldh+Bsglcdh/BL21, pET-28a-rbs4-ltd+Bcldh+Bsglcdh/BL21 and pET-28a-rbs5-ltd+Rjpdh+Ppglcdh/BL21, while 73.6 g·L$^{-1}$ intermediate product ketobutyric acid was detected out in the whole-cell transformation solution of the recombinant bacteria pET-28a-rbs6-ltd+Bsadh+Ppglcdh/BL21, this indicated that the preparation of the α-aminobutyric acid was benefited when the rbs4 and rbs5 sequences were utilized to induce the expression of L-threonine deaminase with glucose dehydrogenase as an enzyme for coenzyme NADH regeneration, wherein the rbs5 sequence was preferred as a ribosome-binding site sequence of the L-threonine deaminase.

Example 10: Production of α-Aminobutyric Acid by Whole-Cell Transformation Conducted After Culturing Recombinant Bacteria pET-28a-rbs5-ltd+Rjpdh+Ppglcdh/BL21 in Different Fermentation Media The recombinant bacteria pET-28a-rbs5-ltd+Rjpdh+Ppglcdh/BL21 were activated by utilizing LB medium, cultured under the conditions of 37° C. and 160 r·min$^{-1}$ overnight and then transferred respectively into 2 L of TB medium, TY medium, TYG medium and GP medium. The inoculation amount was 8%, the culture temperature was 37° C., the rotational speed was 300 r·min$^{-1}$, and the air volume was 1.0 vvm. After 2 h to 3 h of culture, IPTG with a final concentration of 0.5 mM was added, and induction temperature was decreased to 28° C.; after 16 hours of induction, centrifuging was conducted at 8000 r·min$^{-1}$ under 4° C. for 10 minutes, and mycelia were collected; 50 mM PB buffer solution with a pH of 7.5 was utilized to wash the recombinant *Escherichia coli* twice, and the recombinant *Escherichia coli* was resuspended in 50 mM PB buffer solution with a pH value of 7.5, the volume of which was the same as that in culture; 2M L-threonine and 2M glucose were added into the system, transformation was carried out under the conditions of 30° C. and 300 r·min$^{-1}$, and pH was regulated to 7.5 by 1M hydrochloric acid or 5M ammonium hydroxide. After 10 h and 20 h of transformation, samples were extracted respectively, centrifuged and filtered by a 0.22 μm filter membrane and then undergo HPLC analysis. It was discovered that the transformation rates can all reach 98% or more after 20 h of whole-cell transformation from L-threonine utilized by the recombinant bacteria to α-aminobutyric acid following TB medium, TY medium, TYG medium and GP medium fermentation, however, the differences between the transformation rates were great after 10 h, and the transformation rates were respectively 47%, 62%, 66% and 53%, therefore it was determined that the best fermentation medium was the TYG medium, the final yield of gluconic acid reaches 390.8 g·L$^{-1}$ the yield of the α-aminobutyric acid reaches 204 g·L$^{-1}$, and the space-time yield of the α-aminobutyric acid was 10.2 g·L$^{-1}$·h$^{-1}$.

To sum up, the present invention could achieve a good effect by adopting the following means: in front of the L-threonine deaminase gene, there were a promoter carried by a plasmid vector itself and an RBS sequence designed for the L-threonine deaminase gene and the plasmid vector and having expression intensity lower than that of an RBS of the plasmid vector itself; the L-threonine deaminase gene and the L-amino acid dehydrogenase gene were connected through the RBS carried by the plasmid vector itself; and in front of the dehydrogenase gene for providing cofactor NADH cycle, there were a promoter designed for the dehydrogenase gene for providing cofactor NADH cycle and the plasmid vector and an RBS sequence having expression intensity higher than or equal to that of the RBS of the plasmid vector itself.

The recombinant bacterium single-cell factory of the present invention could obtain a better balanced rate from L-threonine to an intermediate product ketobutyric acid and from the ketobutyric acid to α-aminobutyric acid, the accumulation of the intermediate product ketobutyric acid could not be caused, and therefore reaction inhibition could not be caused. Moreover, the recombinant bacterium single-cell factory did not need an exogenously added cofactor, and, in comparison with other methods, reduced the paths via which a substrate got into or out of cells or diffuses, thus increasing the transformation rate.

What is claimed is:

1. A recombinant *Escherichia* bacterium single-cell factory for efficiently synthesizing alpha-aminobutyric acid, wherein said recombinant bacterium single-cell factory comprises a recombinant co-expression plasmid vector comprising
   [i] a ribosome binding site (RBS) sequence operably linked to an L-threonine deaminase gene;
   [ii] an L-amino acid dehydrogenase gene; and
   [iii] a dehydrogenase gene for providing cofactor NADH cycle;
   wherein said RBS sequence is optimized for controlling expression level in *Escherichia*.

2. The recombinant *Escherichia* bacterium single-cell factory according to claim 1, characterized in that excessive accumulation of an intermediate product, ketobutyric acid, does not occur in the recombinant bacterium single-cell factory.

3. The recombinant *Escherichia* bacterium single-cell factory according to claim 1, wherein the expression of the genes of [i]-[iii] is controlled via promoter, RBS sequence optimization, enhancer, terminator and/or silencer optimization.

4. The recombinant *Escherichia* bacterium single-cell factory according to claim 1, characterized in that a construction method for the recombinant bacterium single-cell factory comprises:

(1) according to gene sequences of a promoter and the L-threonine deaminase, designing different intensities of RBS sequences to control the expression level of the L-threonine deaminase, so as to control the rate of transformation from the L-threonine to the ketobutyric acid;

(2) controlling a rate of supplying the cofactor NADH, wherein the expression level of the dehydrogenase for providing cofactor NADH cycle is mainly controlled by optimizing a promoter and an RBS sequence, so as to control the regeneration rate of the cofactor NADH; and (3) connecting the RBS-optimized L-threonine deaminase gene, the L-amino acid dehydrogenase gene, the promoters and the RBS-optimized dehydrogenase gene for providing cofactor NADH cycle in sequence to construct the recombinant co-expression vector, and transforming the recombinant co-expression vector into a host bacteria to construct the genetically engineered bacterium single-cell factory.

5. The recombinant *Escherichia* bacterium single-cell factory according to claim 1, characterized in that:

[a] the plasmid vector comprises a promoter and an RBS sequence designed for the L-threonine deaminase gene in front of the L-threonine deaminase gene, and wherein the optimized RBS sequence decreases the expression level compared to when the RBS sequence is not optimized;

[b] the L-threonine deaminase gene and the L-amino acid dehydrogenase gene are connected through a RBS sequence; and

[c] the plasmid vector comprises a promoter and a RBS sequence in front of the dehydrogenase gene for providing cofactor NADH cycle, and wherein the optimized RBS sequence increases the expression level compared to when the RBS sequence is not optimized.

6. The recombinant *Escherichia* bacterium single-cell factory according to claim 1, characterized in that the host bacteria are *Escherichia coli*.

7. The recombinant bacterium single-cell factory according to claim 1, characterized in that the plasmid vector is a commercially purchasable plasmid vector or a plasmid vector that has been reconstructed.

8. The recombinant bacterium single-cell factory according to claim 1, characterized in that the L-threonine deaminase is *Escherichia coli*-derived L-threonine deaminase.

9. The recombinant bacterium single-cell factory according to claim 1, characterized in that the L-amino acid dehydrogenase is *bacillus*-derived L-leucine dehydrogenase, *bacillus*-derived L-alanine dehydrogenase, *streptomyces*-derived L-valine dehydrogenase and *rhodococcus*-derived L-phenylalanine dehydrogenase.

10. The recombinant *Escherichia* bacterium single-cell factory according to claim 1, characterized in that the dehydrogenase for providing cofactor NADH cycle is formate dehydrogenase of *Candida boidinii*, glucose dehydrogenase of *Bacillus subtilis* and glucose dehydrogenase of *Pseudomonas putida*.

11. The recombinant *Escherichia* bacterium single-cell factory according to claim 5, characterized in that the host is *Escherichia coli*; the promoter in front of the L-threonine deaminase gene is a T7 promoter; wherein the RBS sequence connected directly in front of the L-threonine deaminase gene is any one of sequences set forth in SEQ ID NO:1 to SEQ ID NO:6; and the L-threonine deaminase gene and the L-amino acid dehydrogenase gene are connected through an RBS with a sequence set forth in SEQ ID NO:22.

12. The recombinant *Escherichia* bacterium single-cell factory according to claim 11, characterized in that the promoter in front of the dehydrogenase gene for providing cofactor NADH cycle is a tac promoter, and the RBS sequence in front of the dehydrogenase gene for providing cofactor NADH cycle is any one of sequences set forth in SEQ ID NO:33 to SEQ ID NO:39.

13. A method for synthesizing α-aminobutyric acid by fermentation, comprising fermenting the recombinant bacterium single-cell factory according to claim 1.

14. A method for synthesizing alpha-aminobutyric acid, ketobutyric acid or accessory products related thereto by fermentation, comprising fermenting the recombinant bacterium single-cell factory according to claim 1.

* * * * *

SEQUENCE LISTING

<160> NUMBER OF SEQ ID NOS: 49

<210> SEQ ID NO 1
<211> LENGTH: 34
<212> TYPE: DNA
<213> ORGANISM: Artificial Sequence
<220> FEATURE:
<223> OTHER INFORMATION: Synthetic DNA

<400> SEQUENCE: 1
agtaacaatt tcagcaccgt ttctataacc taat                              34

<210> SEQ ID NO 2
<211> LENGTH: 34
<212> TYPE: DNA
<213> ORGANISM: Artificial Sequence
<220> FEATURE:
<223> OTHER INFORMATION: Synthetic DNA

<400> SEQUENCE: 2
gaaacgcaag aattaactac gacaaactcg ggaa                              34

<210> SEQ ID NO 3
<211> LENGTH: 35
<212> TYPE: DNA
<213> ORGANISM: Artificial Sequence
<220> FEATURE:
<223> OTHER INFORMATION: Synthetic DNA

<400> SEQUENCE: 3
actttctaaa tacctctacc tactctctat aaccc                             35

<210> SEQ ID NO 4
<211> LENGTH: 35
<212> TYPE: DNA
<213> ORGANISM: Artificial Sequence
<220> FEATURE:
<223> OTHER INFORMATION: Synthetic DNA

<400> SEQUENCE: 4
taaaatcaca tccaatttac tacggaaata tccac                             35

<210> SEQ ID NO 5
<211> LENGTH: 33
<212> TYPE: DNA
<213> ORGANISM: Artificial Sequence
<220> FEATURE:
<223> OTHER INFORMATION: Synthetic DNA

<400> SEQUENCE: 5
ttaagcaata aaatatatac ttacggttta caa                               33

<210> SEQ ID NO 6
<211> LENGTH: 31
<212> TYPE: DNA
<213> ORGANISM: Artificial Sequence
<220> FEATURE:
<223> OTHER INFORMATION: Synthetic DNA

<400> SEQUENCE: 6
aaacttcctc caacacctac ggttctataa a                           31

<210> SEQ ID NO 7
<211> LENGTH: 60
<212> TYPE: DNA
<213> ORGANISM: Artificial Sequence
<220> FEATURE:
<223> OTHER INFORMATION: Synthetic DNA

<400> SEQUENCE: 7
gctctagaag taacaatttc agcaccgttt ctataaccta atatggctga ctcgcaaccc    60

<210> SEQ ID NO 8
<211> LENGTH: 60
<212> TYPE: DNA
<213> ORGANISM: Artificial Sequence
<220> FEATURE:
<223> OTHER INFORMATION: Synthetic DNA

<400> SEQUENCE: 8
gctctagaga aacgcaagaa ttaactacga caaactcggg aaatggctga ctcgcaaccc    60

<210> SEQ ID NO 9
<211> LENGTH: 61
<212> TYPE: DNA
<213> ORGANISM: Artificial Sequence
<220> FEATURE:
<223> OTHER INFORMATION: Synthetic DNA

<400> SEQUENCE: 9
gctctagaac tttctaaata cctctaccta ctctctataa cccatggctg actcgcaacc    60
c                                                                  61

<210> SEQ ID NO 10
<211> LENGTH: 61
<212> TYPE: DNA
<213> ORGANISM: Artificial Sequence
<220> FEATURE:
<223> OTHER INFORMATION: Synthetic DNA

<400> SEQUENCE: 10
gctctagata aaatcacatc caatttacta cggaaatatc cacatggctg actcgcaacc    60
c                                                                  61

<210> SEQ ID NO 11
<211> LENGTH: 59
<212> TYPE: DNA
<213> ORGANISM: Artificial Sequence
<220> FEATURE:
<223> OTHER INFORMATION: Synthetic DNA

<400> SEQUENCE: 11
gctctagatt aagcaataaa atatatactt acggtttaca aatggctgac tcgcaaccc    59

<210> SEQ ID NO 12
<211> LENGTH: 57

<212> TYPE: DNA
<213> ORGANISM: Artificial Sequence
<220> FEATURE:
<223> OTHER INFORMATION: Synthetic DNA

<400> SEQUENCE: 12
gctctagaaa acttcctcca acacctacgg ttctataaaa tggctgactc gcaaccc       57

<210> SEQ ID NO 13
<211> LENGTH: 30
<212> TYPE: DNA
<213> ORGANISM: Artificial Sequence
<220> FEATURE:
<223> OTHER INFORMATION: Synthetic DNA

<400> SEQUENCE: 13
cgggatcctt aacccgccaa aaagaacctg       30

<210> SEQ ID NO 14
<211> LENGTH: 39
<212> TYPE: DNA
<213> ORGANISM: Artificial Sequence
<220> FEATURE:
<223> OTHER INFORMATION: Synthetic DNA

<400> SEQUENCE: 14
cgggatccaa ggagatatac atgacattag aaatcttcg       39

<210> SEQ ID NO 15
<211> LENGTH: 28
<212> TYPE: DNA
<213> ORGANISM: Artificial Sequence
<220> FEATURE:
<223> OTHER INFORMATION: Synthetic DNA

<400> SEQUENCE: 15
cgagctctta gcgacggcta ataatatc       28

<210> SEQ ID NO 16
<211> LENGTH: 39
<212> TYPE: DNA
<213> ORGANISM: Artificial Sequence
<220> FEATURE:
<223> OTHER INFORMATION: Synthetic DNA

<400> SEQUENCE: 16
cgggatccaa ggagatatac atgactctca ccgcggaac       39

<210> SEQ ID NO 17
<211> LENGTH: 26
<212> TYPE: DNA
<213> ORGANISM: Artificial Sequence
<220> FEATURE:
<223> OTHER INFORMATION: Synthetic DNA

<400> SEQUENCE: 17
cgagctccta cctggctgca gcgatg       26

<210> SEQ ID NO 18
<211> LENGTH: 38
<212> TYPE: DNA
<213> ORGANISM: Artificial Sequence
<220> FEATURE:
<223> OTHER INFORMATION: Synthetic DNA

<400> SEQUENCE: 18
cgggatccaa ggagatatac atgatcatag gggttcct                               38

<210> SEQ ID NO 19
<211> LENGTH: 27
<212> TYPE: DNA
<213> ORGANISM: Artificial Sequence
<220> FEATURE:
<223> OTHER INFORMATION: Synthetic DNA

<400> SEQUENCE: 19
cgagctctta agcacccgcc acagatg                                           27

<210> SEQ ID NO 20
<211> LENGTH: 40
<212> TYPE: DNA
<213> ORGANISM: Artificial Sequence
<220> FEATURE:
<223> OTHER INFORMATION: Synthetic DNA

<400> SEQUENCE: 20
cgggatccaa ggagatatac atggtgaccg acgtaaacgg                             40

<210> SEQ ID NO 21
<211> LENGTH: 27
<212> TYPE: DNA
<213> ORGANISM: Artificial Sequence
<220> FEATURE:
<223> OTHER INFORMATION: Synthetic DNA

<400> SEQUENCE: 21
cgagctctca cggccgggga cgggcct                                           27

<210> SEQ ID NO 22
<211> LENGTH: 6
<212> TYPE: DNA
<213> ORGANISM: Artificial Sequence
<220> FEATURE:
<223> OTHER INFORMATION: Synthetic DNA

<400> SEQUENCE: 22 aaggag                                                                  6

<210> SEQ ID NO 23
<211> LENGTH: 28
<212> TYPE: DNA
<213> ORGANISM: Artificial Sequence
<220> FEATURE:
<223> OTHER INFORMATION: Synthetic DNA

<400> SEQUENCE: 23
cgggatccat gtatccggat ttaaaagg                                          28

<210> SEQ ID NO 24
<211> LENGTH: 28
<212> TYPE: DNA
<213> ORGANISM: Artificial Sequence
<220> FEATURE:
<223> OTHER INFORMATION: Synthetic DNA

<400> SEQUENCE: 24
cccaagcttt taaccgcggc ctgcctgg                                          28

<210> SEQ ID NO 25
<211> LENGTH: 30
<212> TYPE: DNA
<213> ORGANISM: Artificial Sequence
<220> FEATURE:
<223> OTHER INFORMATION: Synthetic DNA

<400> SEQUENCE: 25
acatgcatgc cgatcccgcg aaattaatac                                    30

<210> SEQ ID NO 26
<211> LENGTH: 27
<212> TYPE: DNA
<213> ORGANISM: Artificial Sequence
<220> FEATURE:
<223> OTHER INFORMATION: Synthetic DNA

<400> SEQUENCE: 26
gaagatcttt aaccgcggcc tgcctgg                                       27

<210> SEQ ID NO 27
<211> LENGTH: 30
<212> TYPE: DNA
<213> ORGANISM: Artificial Sequence
<220> FEATURE:
<223> OTHER INFORMATION: Synthetic DNA

<400> SEQUENCE: 27
cgggatccat gagcactgaa ggtgcgaacc                                    30

<210> SEQ ID NO 28
<211> LENGTH: 29
<212> TYPE: DNA
<213> ORGANISM: Artificial Sequence
<220> FEATURE:
<223> OTHER INFORMATION: Synthetic DNA

<400> SEQUENCE: 28
cccaagcttt tactcggcta atttgtaag                                     29

<210> SEQ ID NO 29
<211> LENGTH: 28
<212> TYPE: DNA
<213> ORGANISM: Artificial Sequence
<220> FEATURE:
<223> OTHER INFORMATION: Synthetic DNA

<400> SEQUENCE: 29
gaagatcttt actcggctaa tttgtaag                                      28

<210> SEQ ID NO 30
<211> LENGTH: 31
<212> TYPE: DNA
<213> ORGANISM: Artificial Sequence
<220> FEATURE:
<223> OTHER INFORMATION: Synthetic DNA

<400> SEQUENCE: 30
accgggatcc atgaaaatcg ttctggttct g                                  31

<210> SEQ ID NO 31
<211> LENGTH: 30
<212> TYPE: DNA
<213> ORGANISM: Artificial Sequence
<220> FEATURE:
<223> OTHER INFORMATION: Synthetic DNA

<400> SEQUENCE: 31
cgcgtcgact tattttttgt cgtgtttacc                                    30

<210> SEQ ID NO 32
<211> LENGTH: 29
<212> TYPE: DNA
<213> ORGANISM: Artificial Sequence
<220> FEATURE:
<223> OTHER INFORMATION: Synthetic DNA

<400> SEQUENCE: 32
gaagatcttt atttttttgtc gtgtttacc                              29

<210> SEQ ID NO 33
<211> LENGTH: 32
<212> TYPE: DNA
<213> ORGANISM: Artificial Sequence
<220> FEATURE:
<223> OTHER INFORMATION: Synthetic DNA

<400> SEQUENCE: 33
gtacgcaaga atacttaact acggttagag gg                           32

<210> SEQ ID NO 34
<211> LENGTH: 32
<212> TYPE: DNA
<213> ORGANISM: Artificial Sequence
<220> FEATURE:
<223> OTHER INFORMATION: Synthetic DNA

<400> SEQUENCE: 34
gtcatagaaa aatttaacct acggttacag gg                           32

<210> SEQ ID NO 35
<211> LENGTH: 32
<212> TYPE: DNA
<213> ORGANISM: Artificial Sequence
<220> FEATURE:
<223> OTHER INFORMATION: Synthetic DNA

<400> SEQUENCE: 35
ctcatagata gaaataacct acggttacag gg                           32

<210> SEQ ID NO 36
<211> LENGTH: 35
<212> TYPE: DNA
<213> ORGANISM: Artificial Sequence
<220> FEATURE:
<223> OTHER INFORMATION: Synthetic DNA

<400> SEQUENCE: 36
acaaatactc tataaaaaaa actacggtta gaata                        35

<210> SEQ ID NO 37
<211> LENGTH: 34
<212> TYPE: DNA
<213> ORGANISM: Artificial Sequence
<220> FEATURE:
<223> OTHER INFORMATION: Synthetic DNA

<400> SEQUENCE: 37
ctcatctaat acaatacaaa ctacggttag aaca                         34

<210> SEQ ID NO 38
<211> LENGTH: 35
<212> TYPE: DNA
<213> ORGANISM: Artificial Sequence
<220> FEATURE:
<223> OTHER INFORMATION: Synthetic DNA

<400> SEQUENCE: 38
aatctacaat aaatctcaca actacggtta taata    35

<210> SEQ ID NO 39
<211> LENGTH: 31
<212> TYPE: DNA
<213> ORGANISM: Artificial Sequence
<220> FEATURE:
<223> OTHER INFORMATION: Synthetic DNA

<400> SEQUENCE: 39
tgttaaacaa ggtccaacta cggttaacac a    31

<210> SEQ ID NO 40
<211> LENGTH: 59
<212> TYPE: DNA
<213> ORGANISM: Artificial Sequence
<220> FEATURE:
<223> OTHER INFORMATION: Synthetic DNA

<400> SEQUENCE: 40
cccaagcttg tacgcaagaa tacttaacta cggttagagg gatgaagatc gttttagtc    59

<210> SEQ ID NO 41
<211> LENGTH: 59
<212> TYPE: DNA
<213> ORGANISM: Artificial Sequence
<220> FEATURE:
<223> OTHER INFORMATION: Synthetic DNA

<400> SEQUENCE: 41
cccaagcttg tcatagaaaa atttaaccta cggttacagg gatgaagatc gttttagtc    59

<210> SEQ ID NO 42
<211> LENGTH: 59
<212> TYPE: DNA
<213> ORGANISM: Artificial Sequence
<220> FEATURE:
<223> OTHER INFORMATION: Synthetic DNA

<400> SEQUENCE: 42
cccaagcttc tcatagatag aaataaccta cggttacagg gatgaagatc gttttagtc    59

<210> SEQ ID NO 43
<211> LENGTH: 62
<212> TYPE: DNA
<213> ORGANISM: Artificial Sequence
<220> FEATURE:
<223> OTHER INFORMATION: Synthetic DNA

<400> SEQUENCE: 43
cccaagctta caaatactct ataaaaaaaa ctacggttag aataatgaag atcgttttag    60
tc    62

<210> SEQ ID NO 44
<211> LENGTH: 61
<212> TYPE: DNA
<213> ORGANISM: Artificial Sequence
<220> FEATURE:
<223> OTHER INFORMATION: Synthetic DNA

<400> SEQUENCE: 44
cccaagcttc tcatctaata caatacaaac tacggttaga acaatgaaga tcgttttagt    60

```
c                                                               61

<210> SEQ ID NO 45
<211> LENGTH: 62
<212> TYPE: DNA
<213> ORGANISM: Artificial Sequence
<220> FEATURE:
<223> OTHER INFORMATION: Synthetic DNA

<400> SEQUENCE: 45
cccaagctta atctacaata aatctcacaa ctacggttat aataatgaag atcgttttag      60
tc                                                                    62

<210> SEQ ID NO 46
<211> LENGTH: 58
<212> TYPE: DNA
<213> ORGANISM: Artificial Sequence
<220> FEATURE:
<223> OTHER INFORMATION: Synthetic DNA

<400> SEQUENCE: 46
cccaagcttt gttaaacaag gtccaactac ggttaacaca atgaagatcg ttttagtc        58

<210> SEQ ID NO 47
<211> LENGTH: 28
<212> TYPE: DNA
<213> ORGANISM: Artificial Sequence
<220> FEATURE:
<223> OTHER INFORMATION: Synthetic DNA

<400> SEQUENCE: 47
cgggatcctt atttcttatc gtgtttac                                        28

<210> SEQ ID NO 48
<211> LENGTH: 28
<212> TYPE: DNA
<213> ORGANISM: Artificial Sequence
<220> FEATURE:
<223> OTHER INFORMATION: Synthetic DNA

<400> SEQUENCE: 48
catgcatgct gacaattaat catcggct                                        28

<210> SEQ ID NO 49
<211> LENGTH: 25
<212> TYPE: DNA
<213> ORGANISM: Artificial Sequence
<220> FEATURE:
<223> OTHER INFORMATION: Synthetic DNA

<400> SEQUENCE: 49
gaagatctag agtttgtaga aacgc                                           25
```